US011307138B2

(12) United States Patent
Hattingh (10) Patent No.: US 11,307,138 B2
(45) Date of Patent: Apr. 19, 2022

(54) TESTING METHOD FOR RESIDUAL ORGANIC COMPOUNDS IN A LIQUID SAMPLE

(71) Applicant: Paul Hattingh, Lago Vista, TX (US)

(72) Inventor: Paul Hattingh, Lago Vista, TX (US)

(*) Notice: Subject to any disclaimer, the term of this patent is extended or adjusted under 35 U.S.C. 154(b) by 0 days.

(21) Appl. No.: 16/817,247

(22) Filed: Mar. 12, 2020

(65) Prior Publication Data

US 2020/0292444 A1  Sep. 17, 2020

Related U.S. Application Data

(60) Provisional application No. 62/816,993, filed on Mar. 12, 2019.

(51) Int. Cl.
*G01N 21/33* (2006.01)
*G01N 21/03* (2006.01)
(Continued)

(52) U.S. Cl.
CPC ............ *G01N 21/33* (2013.01); *G01N 1/28* (2013.01); *G01N 21/0332* (2013.01);
(Continued)

(58) Field of Classification Search
CPC .... G01N 21/03; G01N 21/0332; G01N 21/05; G01N 21/25; G01N 21/251; G01N 21/253; G01N 21/255; G01N 21/27; G01N 21/272; G01N 21/274; G01N 21/29; G01N 21/31; G01N 21/33; G01N 21/59; G01N 21/85;
(Continued)

(56) References Cited

U.S. PATENT DOCUMENTS 2,824,968 A * 2/1958 Sparks, Jr. ............. G01N 21/05
250/429
3,255,575 A * 6/1966 Roberts ................... G01N 1/28
95/24
(Continued)

OTHER PUBLICATIONS

Richmond, M.L. et al., "Separation of Carbohydrates in Dairy Products by High Performance Liquid Chromatography," 1982, Journal of Dairy Science, 65: 1394-1400 (Year: 1982).*
(Continued)

*Primary Examiner* — Gordon J Stock, Jr.
(74) *Attorney, Agent, or Firm* — Waller Lansden Dortch & Davis LLP; Blake M. Bernard (57) ABSTRACT

A method and system for testing a liquid sample for an organic compound is disclosed, the method including the steps of collecting the liquid sample from a liquid source; transmitting light having a wavelength of between about 190 nanometers and about 310 nanometers into the liquid sample; measuring absorption/transmission of the light by the organic compound in the liquid sample; and determining a concentration of the organic compound within the liquid sample based on the absorption/transmission of the light by the organic compound. The system can include a spectrophotometer for measuring the absorption of UV light by the organic compound, an ion exchange column for removing ion contaminants from the liquid sample, and a vacuum degasser unit for removing gases and other impurities from the liquid sample.

18 Claims, 4 Drawing Sheets

(51) Int. Cl.
*G01N 33/18* (2006.01)
*G01N 1/28* (2006.01)
*G01N 21/59* (2006.01)
*G01N 21/85* (2006.01)
*G01N 21/31* (2006.01)
*C02F 5/12* (2006.01)
*C02F 101/30* (2006.01)

(52) U.S. Cl.
CPC ............ *G01N 21/59* (2013.01); *G01N 21/85* (2013.01); *G01N 33/1826* (2013.01); *C02F 5/12* (2013.01); *C02F 2101/30* (2013.01); *C02F 2303/08* (2013.01); *G01N 2021/3125* (2013.01); *G01N 2021/335* (2013.01); *G01N 2021/8571* (2013.01)

(58) Field of Classification Search
CPC ... G01N 2021/3118; G01N 2021/3122; G01N 2021/3124; G01N 2021/3129; G01N 2021/3185; G01N 2021/3188; G01N 2021/3196; G01N 2021/335; G01N 2021/5969; G01N 2021/5973; G01N 2021/3133; G01N 2021/3137; G01N 2021/8571; G01N 2021/054; G01N 1/28; G01N 1/38; G01N 1/40; G01N 1/4005; G01N 2001/383; G01N 2001/386; G01N 2001/4011; G01N 2001/4016; G01N 33/1826; G01N 33/183; G01N 33/184; G01N 33/1846; G01N 33/188; G01N 33/1893; G01N 2021/3125; C02F 5/10; C02F 5/12; C02F 2303/08; C02F 5/00; C02F 5/02; C02F 5/025; C02F 5/04; C02F 5/06; C02F 5/08; C02F 5/083; C02F 5/086; C02F 5/105; C02F 5/125; C02F 5/14; C02F 5/145; C02F 2101/30; F22B 37/38; F22B 37/42; F22B 37/423; F22B 37/426; F22B 37/56
See application file for complete search history.

(56) References Cited

U.S. PATENT DOCUMENTS

| | | | | |
|---|---|---|---|---|
| 3,382,984 A * | 5/1968 | Kuss | ................. | B01D 27/04 210/448 |
| 3,458,453 A * | 7/1969 | Kautsky | ................. | C10G 7/10 252/392 |
| 3,679,898 A * | 7/1972 | Compton | ................. | G01N 21/85 250/304 |
| 4,498,774 A * | 2/1985 | Yeung | ................. | G01N 30/74 356/368 |
| 4,816,303 A * | 3/1989 | Kroenke | ................. | C09K 8/54 106/14.15 |
| 4,889,593 A | 12/1989 | Tikka et al. | | |
| 5,098,562 A | 3/1992 | Shibata et al. | | |
| 5,169,563 A * | 12/1992 | Katayama | ................. | C02F 5/12 252/389.53 |
| 5,242,602 A * | 9/1993 | Richardson | ........ | G01N 21/8507 210/745 |
| 5,272,346 A * | 12/1993 | Kaplan | ............. | G01N 33/1826 250/373 |
| 5,278,074 A * | 1/1994 | Rao | ................. | G01N 33/1826 436/52 |
| 5,420,432 A | 5/1995 | Manook et al. | | |
| 5,550,630 A | 8/1996 | Chrastil | | |
| 5,654,198 A * | 8/1997 | Carrier | ................. | G01N 21/31 436/164 |
| 5,798,271 A | 8/1998 | Godec et al. | | |
| 5,820,823 A * | 10/1998 | Godec | ................. | G01N 27/06 422/78 |
| 6,040,406 A * | 3/2000 | Carrier | ................. | C02F 1/56 252/175 |
| 7,229,833 B1 * | 6/2007 | Andersson | ............ | G01N 21/33 436/73 |
| 8,023,118 B2 * | 9/2011 | Takahashi | ............. | G01N 21/00 356/451 |
| 9,222,921 B2 * | 12/2015 | Saini | ................. | G01N 30/88 |
| 9,352,993 B2 * | 5/2016 | Nakajima | ............. | F22B 35/10 |
| 2004/0188352 A1 * | 9/2004 | Dey | ................. | B01D 61/04 210/652 |
| 2009/0122307 A1 * | 5/2009 | Chai | ................. | G01N 21/33 356/300 |
| 2009/0316119 A1 * | 12/2009 | Parekh | ............... | G03F 7/70341 355/30 |
| 2012/0178175 A1 | 7/2012 | Crosman | | |
| 2014/0091039 A1 * | 4/2014 | Dueck | ................. | B01D 61/58 210/638 |
| 2014/0260708 A1 * | 9/2014 | Harrell | ............... | G01N 33/2823 73/866 |
| 2016/0115061 A1 * | 4/2016 | Ukai | ................. | C02F 9/00 210/696 |
| 2016/0123882 A1 * | 5/2016 | Gilmore | ............... | G01N 21/645 250/227.11 |
| 2016/0370329 A1 * | 12/2016 | Jayaraman | ............... | B01J 39/07 |
| 2017/0363592 A1 * | 12/2017 | Pohl | ................. | B01J 39/26 |
| 2018/0030345 A1 * | 2/2018 | Gill | ................. | C23F 11/08 |
| 2018/0172621 A1 * | 6/2018 | Cheng | ................. | G01N 27/49 |
| 2018/0273412 A1 * | 9/2018 | Hall | ................. | C02F 9/00 |

OTHER PUBLICATIONS

PCT/US2020/022428 International Search Report and Written Opinion, 10 pages, dated Jul. 3, 2020.

* cited by examiner

TESTING METHOD FOR RESIDUAL ORGANIC COMPOUNDS IN A LIQUID SAMPLE

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of U.S. Patent Application No. 62/816,993 filed Mar. 12, 2019 entitled TESTING METHOD FOR RESIDUAL ORGANIC COMPOUNDS IN A WATER SAMPLE, which is hereby incorporated by reference in its entirety.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to testing liquid samples, and particularly water samples, for the presence of certain organic compounds within the sample.

More specifically, the disclosure relates to testing for residual organic compounds in a water sample. One such application for such tests are for testing water samples used in steam boilers for the presence of certain organic compounds, those existing naturally or those added. Various organic compounds may be added to water supplies for various purpose. For instance, some organic compounds can be added to a water supply to help prevent corrosion of metallic parts or systems in which the water supply comes into contact. One such organic compound with anti-corrosion properties is the proprietary organic compound sold as Anodamine® by Anodamine Inc. which can be used to treat steam water cycles in steam boilers or other industrial applications. It can be beneficial to periodically test the residual amount of organic compound additives to the water supply in such industrial systems to ensure a proper or desired amount of the organic compound additive is contained within the water supply.

Conventional testing methods include introducing indicator reagents into a liquid sample that are designed to react with the desired organic chemical component which is the subject of the test. The indicator reagent can produce a residual color or a component as a reaction between the indicator reagent and the chemical of interest. Incremental amounts of the indicator reagent are added to the sample until the colored compound is visible in the testing sample, indicating the presence of the compound. The indicator reagent added forms a colored complex which is proportional in a linear manner to the component of interest. These tests are based upon visibly detecting the intensity of the compound formed between the indicator reagent added and the substance of interest, and certain assumptions based on the relationship between the amount of reagent added and the concentration of the chemical of interest within the sample, such tests may be qualitative in nature, exposed to significant interferences and estimates at best.

What is needed then are improvements in testing for organic chemicals in water/liquid test samples.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the present disclosure is a method of testing a liquid sample for an organic compound, the method including the steps of collecting the liquid sample from a liquid source; transmitting light having a wavelength of between about 190 nanometers and about 310 nanometers into the liquid sample; measuring absorption/transmission of the light by the organic compound in the liquid sample; determining a concentration of the organic compound within the liquid sample based on the absorption/transmission of the light by the organic compound. In some embodiments, the method can further include pumping the liquid sample and passing the liquid sample through a first vacuum degassing channel; passing the liquid sample through a strong acid cation-charged resin column; passing the liquid sample through a second vacuum degassing channel; and illuminating the liquid sample with ultra-violet wavelength light having a wavelength of between about 190 nanometers and about 310 nanometers and measuring the absorption/transmission of the light with a suitable spectrophotometer.

Another aspect of the present disclosure is a system for measuring the concentration of an organic compound in a water/liquid sample, the system including a pump for pumping the liquid sample through the system; an ion exchange column in fluid communication with the pump; and a spectrophotometer in fluid communication with the ion exchange column, the spectrophotometer configured to transmit light having a wavelength of about 190 nanometers to 310 nanometers into the liquid sample and measure the absorption/transmission of the light by the organic compound in the liquid sample. In some embodiments, the system can include a first vacuum degasser channel in fluid communication between the pump and the ion exchange column such that the ion exchange column is in fluid communication with the pump via the first vacuum degasser channel. In some embodiments, the system can further include a second vacuum degasser channel in fluid communication between the ion exchange column and the spectrophotometer such that the ion exchange column is in fluid communication with the spectrophotometer via the second vacuum degasser channel.

One objective of the present disclosure is to accurately and efficiently detect the presence of organic compounds in water/liquid samples without being required to add indicator reagents, such water samples including but not limited to water samples from steam boilers.

Another objective of the present disclosure is to measure the presence of organic compounds in a liquid sample using spectrophotometry techniques across the UV light spectrum.

Another objective of the present disclosure is to remove interferences and contaminants from a liquid sample before the sample is tested for the presence of an organic compound using spectrophotometry techniques.

Numerous other objects, advantages and features of the present disclosure will be readily apparent to those of skill in the art upon a review of the following drawings and description of a preferred embodiment.

DETAILED DESCRIPTION

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

This method and systems disclosed herein allow users to test a liquid or water sample for the presence of organic compounds of interest. The method and systems disclosed herein can be particularly useful in the thermal power industry or any user that uses steam boilers for the purpose of producing steam or condensate to quantitatively measure the residual amount of desired organic components in the water, water vapor, or steam used within such systems. The method can not only be used to measure residual quantities of a specific organic compound, such as the proprietary anti-corrosion chemical sold under the name Anodamine®, but also to measure any other naturally occurring organic compounds, like humic acids and polysaccharides, or the total organic compounds (TOC) present in the sample. The method, whilst initially developed for the measurement of the organic, surface-active metal corrosion inhibiting product (Anodamine®), may also be tailored to allow for the measurement of most saturated and unsaturated organics, especially those with aliphatic long-chain nitrogen-containing functional groups.

The methods and systems of the present disclosure can help remove the need for reagents, can be low-cost, and can help provide a rapid determination of the presence of organic components in a water or liquid sample. The methods and systems disclosed herein are an industry-first methodology for the measurement of organic components, specifically with light in the UV spectrum (190-310 nm range). The wavelength selected for the test can be based upon the organic type, architecture and bond functionality of the target organic component. Each organic structure would require its own UV wavelength calibration curve to calculate concentrations of the specific organic compound in a test water or liquid sample based on measured light absorption by the organic compound in the sample.

The method allows for the residual measurement of both the Anodamine® high-pressure product grade as well as the Anodamine® low-pressure product grade. The method was conducted, optimized, and validated using specific hardware and software, discussed below. The method was also validated using a specific analytical instrumentational configuration and technique as detailed herein.

Instrumentation and Methodology

One aspect of the present disclosure, as shown in FIGS. 1-4 is a system 10 for measuring the concentration of an organic compound in a water/liquid sample 12, the system 10 including a pump 14 for pumping liquid from the liquid sample 12 through the system 10; an ion exchange column 16 in fluid communication with the pump 14; and a spectrophotometer 18 in fluid communication with the ion exchange column 16, the spectrophotometer 18 configured to transmit light 26 having a wavelength of about 190 nanometers to 310 nanometers into the liquid sample 12 and measure the absorption/transmission of the light 20 by the organic compound in the liquid sample 12. Transmitting light 26 having a wavelength of between about 190 and 310 nanometers can mean that the spectrophotometer 18 can be configured to transmit any singular wavelength of light within the range of 190 to 310 nanometers, any subsets of wavelengths of light between 190 and 310 nanometers, all wavelengths of light between 190 and 310 nanometers, or bands of light wherein a portion of the band of light has wavelengths between 190 and 310 nanometers and a portion of the band of light that is not between 190 and 310 nanometers. In other words, at least a portion of the light transmitted into the liquid sample 12 can have wavelengths of between about 190 and 310 nanometers. The specific wavelengths transmitted through the liquid sample 12 can be tailored depending on the relevant light absorption spectrum of the organic compound of interest.

Figure 1:
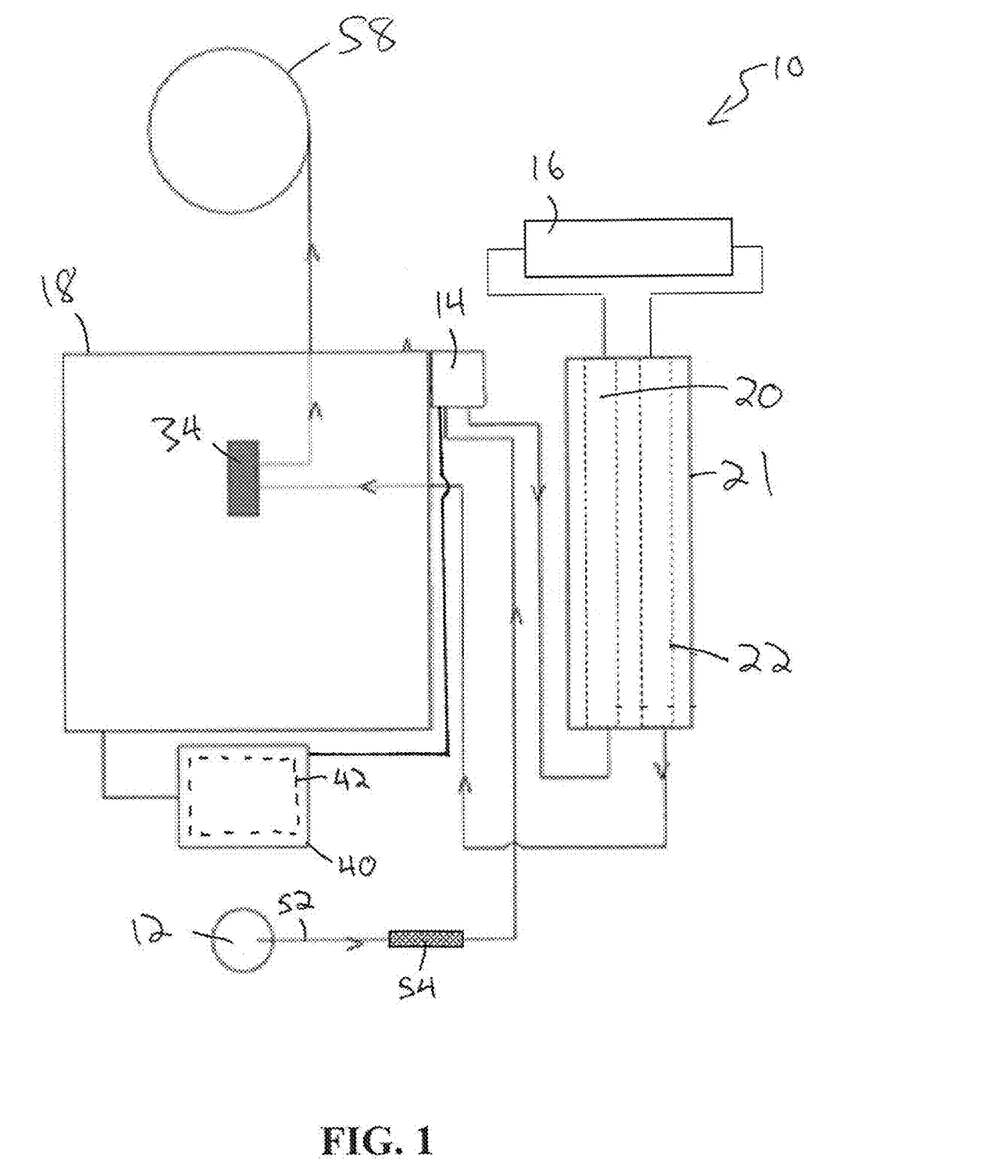
FIG. 1 is schematic drawing of an exemplary embodiment of a testing system of the present disclosure for testing for the presence of an organic compound in a water/liquid test sample.

In some embodiments, the system 10 can include a first vacuum degasser channel 22 in fluid communication between the pump 14 and the ion exchange column 16 such that the ion exchange column 16 is in fluid communication with the pump 14 via the first vacuum degasser channel 20. In some embodiments, the system 10 can further include a second vacuum degasser channel 22 in fluid communication between the ion exchange column 16 and the spectrophotometer 18 such that the ion exchange column 16 is in fluid communication with the spectrophotometer 18 via the second vacuum degasser channel 22.

A certain instrumentational configuration, quality of optics and measurement sensitivity are required for the successful application and method sensitivity that is needed to measure most saturated and unsaturated organics (especially those with aliphatic, long-chain, nitrogen-containing functionalities). The method has been specifically adapted to the Mettler Toledo UV5Bio spectrophotometer, utilizing the additional Mettler Toledo FillPalMini peristaltic pump and optical quartz 50 mm flow-through cell, though any suitable pump/aspirator device and spectrophotometer could be utilized depending on the organic compound of interest. Sample preparation can include the use of a suitably sized ion exchange column 16, and in some embodiments the ion exchange column 16 can include a strong acid, cation-charged resin column for removing cation contaminants including but not limited to sodium, magnesium, calcium, etc. with inline vacuum degasser channels. Depending on the contaminants trying to be removed from the test sample 12, other types of ion exchange resin columns 16 can be utilized to remove such contaminants. All interconnecting tubing, and all wetted parts can be of chemically-resistant fluoropolymer or Teflon-based material. The methods sample aspiration flow rates, wait times, and sample measurements have all been calibrated based upon the specific equipment, optical design, and measurement sensitivity.

Spectrophotometer

Figure 2:
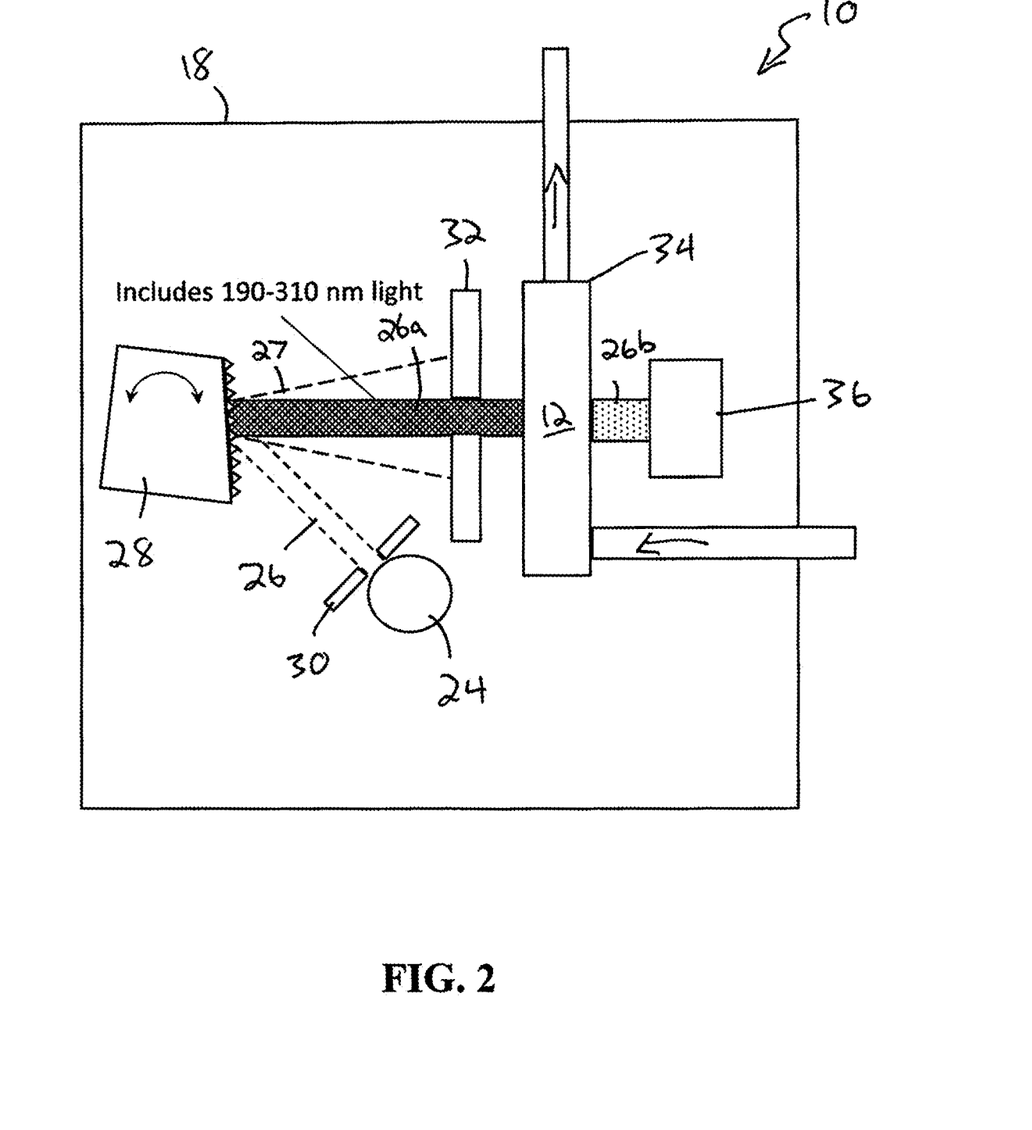
FIG. 2 is a schematic view of an exemplary spectrophotometer which can be utilized in the system of FIG. 1.

One exemplary spectrophotometer configuration is shown in FIG. 2. The spectrophotometer 18 can include a light source 24 and an entrance slit 30 through which the light source 24 passes a beam of light 26 towards a diffraction grating 28. The diffraction grating 28 can refract the light 26 into a light prism 27. The light prism 27 can be directed toward an exit slit 32, the exit 32 allowing only a desired range of light wavelengths to pass through the exit slit 32 and through the sample 12 contained in a quartz cuvette 34. It can be beneficial to use Quartz cuvettes 34 in the system 34 because quartz cuvettes 34 do not absorb UV light, which can help increase the accuracy of the test.

Figure 5:
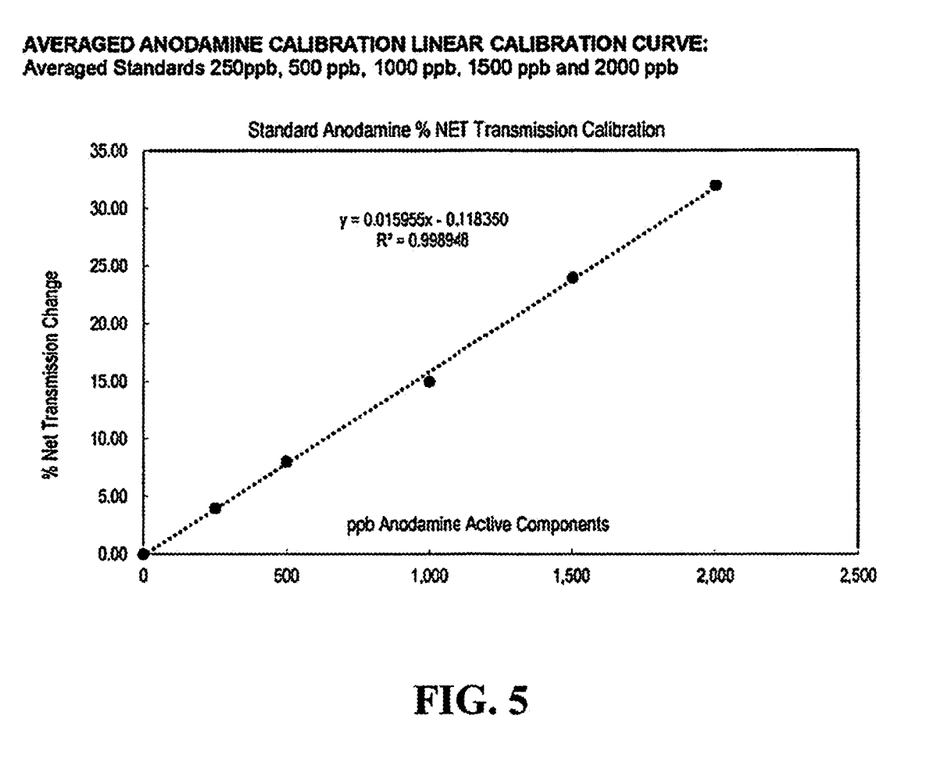
FIG. 5 is a graph of a sample calibration curve which can be used to determine concentrations of organic compounds in a water test sample based on absorption/transmission of light, the example shown in FIG. 5 being for the organic compound Anodamine®.

Absorption of light 26 having a wavelength between about 190 and 310 by organic compounds in the test sample 12 can be measured using a light detector 36 such as a photocell. As light 26 is absorbed by organic compounds in the sample 12, the intensity of the light 26b exiting the sample 12 and the cuvette 34 can be less than the light 26a entering the cuvette, as shown in FIG. 2. The light detector 36 can measure the intensity of light 26 exiting the sample 12. The intensity of the light 26b exiting the cuvette 34 can be compared to the intensity of the light 26a entering the cuvette 34 to determine an absorption percentage or a net transmission change. A calibration curve similar to the one shown in FIG. 5 for an organic compound of interest can be used to determine the concentration of the organic compound of interest in the sample 12 based on the net transmission change percentage measured from the testing system 10. While one spectrophotometer 18 configuration is generally shown in FIG. 2, any suitable spectrophotometer 18 can be utilized in the system 10.

In one embodiment, the Mettler Toledo UV5Bio spectrophotometer can be utilized, which can include a unique reverse optics design, which illuminates the sample with polychromatic light. The wavelength determination is done after the sample and right before the diode array or photo detector 36. With this design the negative effect of ambient room light on the liquid flow path and cuvette 34 and thus the measurement of the sample 12 can be reduced. The benefit of room light immunity allows the sample 12 and the entire flow path to be visible to the operator, thus making any leaks or air bubbles easily detected, all of which could adversely affect the measurements' integrity and sensitivity.

The UV5Bio uses a single, pulsed-Xenon lamp as a light source, which covers the wavelength range from 190-1100 nm and can be programmed to measure absorption of any wavelength or range of wavelengths between 190 and 310 nanometers. The UV5Bio can have a photometric accuracy of about ±0.01 amps, a wavelength accuracy of ±1.0 nanometers, a resolution greater than 1.5, and a stray light rating greater than 2. The pulse of the flash lamp is controlled by the integrated software to ensure that the sample is only illuminated during a measurement. This can help decrease photo-bleaching effects experienced with organic molecules. The pulsed light source does not require a "warm-up" period to achieve a stable reading, which is usually required in a dual-lamp system. This allows the system 10 to operate faster from when the instrument is powered on until a reliable measurement can be made.

The spectrophotometer 18 in some embodiments can measure the entire wavelength spectrum simultaneously. By measuring the entire spectrum, rather than just a single or several wavelengths, the spectrophotometer 18 can allow for multiple measurements of functionality and the detection of contaminants that may occur in the sample 12, and can also be used to calculate a total organic compound concentration, as opposed to a concentration of a single organic compound in the sample 12.

The light detector 36 in some embodiments can have as many as 2048 pixels to simultaneously measure the wavelengths required. This can allow for a significantly tighter wavelength determination compared to an array with less pixels. The dispersion element (diffraction grating) 28 in some embodiments can be held rigidly in place in a single mono-block. This design offers a unique field-application benefit, in that it can help eliminate any vibrational effects on the optical system that would typically be encountered. In other embodiments, the diffraction grating 28 can be rotatable such that the wavelength or range of wavelengths being transmitted into the sample 12 can be adjusted for different uses or applications.

The entire optical train of the spectrophotometer 18 can be set and locked in at factory settings, so that users cannot inadvertently change optical elements, which would drastically alter the results of this method. Changing optics would result in incorrect readings, without the software or operator knowing about the error.

Referring again to FIG. 1, the UV5Bio system is also controlled by PC-based software with restricted user control privileges and simple shortcut menu options. The control system can also govern the timing and functioning of the pump and flow rates of the sample as discussed herein. The control system 40 can be in electrical communication with the pump 14 and the spectrophotometer 18 and can include a user interface 42 which can allow a user to control operation and timing of the system 10, and can optionally allow the user to control optical setting associated with the spectrophotometer 18.

The use of spectrophotometer techniques to measure the presence of organic compounds in a liquid sample 12 can provide significant benefits over conventional testing methods including the use of reagents or indicators which are added to the sample 12 and are designed to produce a color change in the sample to determine the concentration of the organic compound in the sample 12. Spectrophotometry techniques can help increase the consistency, precision, and accuracy of the sample tests to reagent techniques.

Pre-Treatment Strong Acid, Cation Resin Ion-Exchange Column

One issue with spectrophotometry techniques is that contaminants in a testing sample 12 can negatively affect the accuracy of the tests. However, many conventional techniques utilized to remove such contaminants can adversely cause a reaction with the underlying organic compounds that could also negatively affect the accuracy of tests utilizing spectrophotometry techniques. The proprietary pretreatment techniques disclosed herein can sufficiently remove impurities and other contaminants from a liquid sample 12 prior to testing the sample 12 for the presence of desired organic compounds within the sample 12 with spectrophotometry techniques without removing or altering the organic compound of interest within the sample 12.

Figure 4:
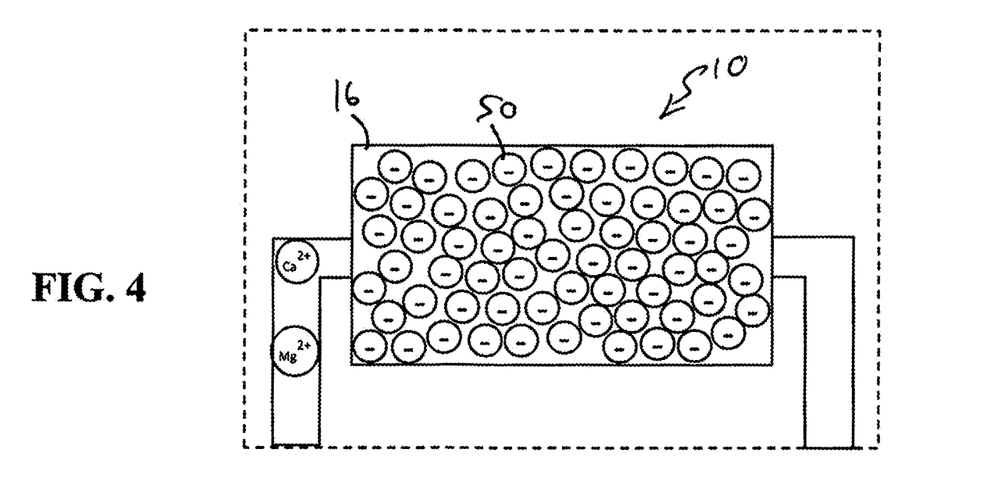
FIG. 4 is a schematic view of an exemplary strong acid cation resin column that can be utilized in the testing system of FIG. 1 to remove cation contaminants from a liquid sample.

Referring again to FIG. 1, one aspect of a pretreatment protocol for the system 10 of the present disclosure is an ion exchange column 16. The ion exchange column 16 can be designed to remove unwanted ion contaminants from a sample 12 prior to testing of the sample 12 with the spectrophotometer 18. In steam boiler systems specifically, the use of a strong acid, cation-charged resin column 16, or a column full or negatively charged semipermeable resin beads 50 as shown in FIG. 4, for sample preparation can help remove common cationic contaminants that are typically known to exist in steam-water cycles. By process of common ion exchange, these cations can be converted to carbonic acid (dissolved carbon dioxide in water), which reduces the sample pH. After the strong acid cation column 16 processing, the sample 12 can then be passed through a vacuum degasser unit 21 as discussed in further detail herein to remove the carbon dioxide in the carbonic acid from the sample 12. Sample flow is as shown in the equipment configuration layout in FIG. 1. In other embodiments, the ion exchange can be an anion-charged exchange column which can remove unwanted anions from a test sample 12 in the event anion contaminants are common in a given application. In still other embodiments, the system 10 can include both a cation-charged resin column and an anion charged resin column in series to remove both cations and anions from the test sample 12 prior to testing with the spectrophotometer.

The strong acid cation-charged resin column 16 in some embodiments can utilize a clear, vertical column with color impregnated, strong acid cation-charged resin. Non-colored, commercially available resin can also be used. For application of this method, and to help ensure reliable, repeatable routine measurements, colored resin can be used. As the strong acid cation-charged resin column becomes exhausted, the resin will change color to alert the user/operator on when resin replacement or regeneration is required. Utilizing exhausted strong acid cation resin offers significant method positive interferences.

In some applications, it is beneficial to periodically regenerate the strong acid cation-charged resin column 16 by passing a solution of strong acid at a concentration between about 2 and 10% through the strong acid cation-charged resin column 16. In some embodiments, regeneration can occur on a daily basis to counter the effects of stagnant water left in the strong acid cation-charged resin column 16, including the release of organics including polysulfates, which can contaminate the system 10 on startup the subsequent day. Similarly, if an anion-charged resin column is used, a solution of sodium hydroxide or another brine solution can be passed through the anion-charged resin column at similar concentrations to recharge the anion-charged resin column. In the case of a cation-charged resin column, daily passing of a strong acid solution through the entire system can provide the added benefit of helping remove any metal particles or other contaminants which may have been deposited on various components of the system, thus helping maintain the cleanliness and efficiency of the system 10.

Pre-Treatment Vacuum Degasser

Figure 3:
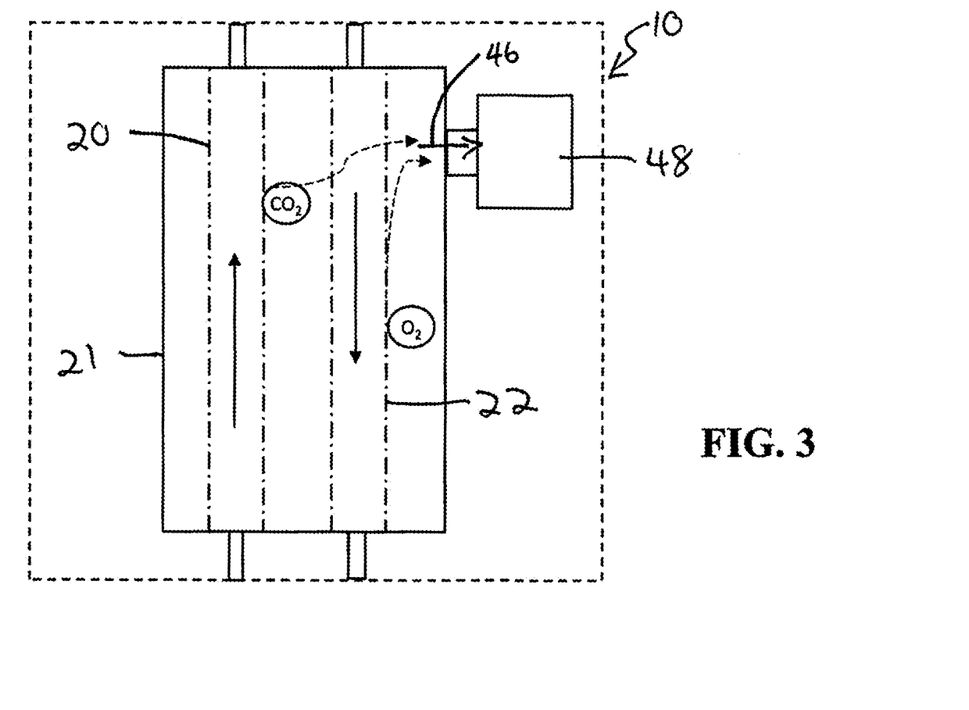
FIG. 3 is a schematic view of an exemplary vacuum degasser unit that can be utilized in the testing system of FIG. 1 to remove gasses and other small particle impurities from a liquid sample.

Referring again to FIG. 1, a vacuum degasser unit 21 can be used for the sample preparation prior to testing with a spectrophotometer 18. The vacuum degasser unit 21 can include two semipermeable tubes or vacuum degasser channels 20 and 22. In some embodiments, the vacuum degasser channels 20 and 22 can be made from a Teflon-based material. The vacuum degasser channels 20 and 22 when exposed to a vacuum pressure 46 via a vacuum pump 48, as shown in FIG. 3, can allow for vacuum removal of certain unwanted contaminants in the sample 12. For example, in some embodiments the vacuum degasser unit 21 can provide for vacuum-based removal of oxygen, carbon dioxide, ammonia, and low molecular weight, short-chain carboxylic acids (like formic acid, acetate, glycolate), which are contaminants typically known to exist in a user's steam water cycle. Such contaminants can negatively affect the results of the testing done with the system 10 as such contaminants can absorb UV light, which can potentially falsely indicate a higher concentration of a desired organic compound within the sample 12. The larger long chain organic compounds that are the target of the test would not be able to pass through the semipermeable tubes of the vacuum degasser channels 20 and 22 and thus would remain in the sample 12.

In some embodiments, the vacuum degasser channels 20 and 22 can be oriented parallel to one another within the vacuum degasser unit 21. The size, shape, and orientation of the semipermeable tubes or channels 20 and 22 can vary in different embodiments. In still other embodiments, separate vacuum degasser devices with individual tubes or channels can be utilized in the system.

The vacuum degasser has also been shown to be especially effective at the removal of low (parts per billion) concentrations of the above contaminants, in the following order of effectiveness: carbon dioxide, oxygen, ammonia, formate, acetate, and glycolate. If not adequately removed, the above contaminants act as positive interferences for the detection method and spectrophotometer.

In some embodiments, both first and second degasser channels 20 and 22 respectively, can be contained in a single vacuum degasser unit 21 connected to a single vacuum pump 48. In other embodiments, each vacuum degasser channel 20 and 22 can be housed in separate vacuum degasser units, each unit having its own vacuum pump 48. In still other embodiments, more than two vacuum degasser channels can be utilized to further remove any unwanted contaminants from the sample 12.

In some embodiments, as shown in FIG. 1, the first vacuum degasser channel 20 can be in fluid communication between the pump 14 and the ion exchange column 16 such that the ion exchange column 16 is in fluid communication with the pump 14 via the first vacuum degasser channel 20. In some embodiments, the second vacuum degasser channel 22 can be in fluid communication between the ion exchange column 16 and the spectrophotometer 18 such that the ion exchange column 16 is in fluid communication with the spectrophotometer 18 via the second vacuum degasser channel 22. The sample 12 can thus be passed through a first vacuum degasser channel 20 to remove unwanted gases, such as carbon dioxide, from the sample prior to the sample entering the ion exchange column 16. Removing such contaminants before the sample 12 enters the ion exchange column 16 can help increase the efficiency of the ion exchange process. The sample 12 can then be passed through a second vacuum degasser channel 22 to remove additional carbon dioxide and other contaminants produced from the ion exchange occurring the ion exchange column 16.

Referring again to FIG. 1, in some embodiments, the pump can include a suction line 52 which can be placed in the liquid sample 12 to draw the liquid sample 12 into the system 10 via the pump 14. In some embodiments, the liquid suction line 52 can include a filter media 54 which can be oriented such that the liquid sample passes through the filter media 54 as the liquid sample 12 is drawn into the system 10. The filter media 54 in some embodiments can be 0.1 to 0.3 micron filter such that particles larger than the filter size of the filter media 54 will be effectively filtered out of the sample 12 prior to the sample 12 entering the other components of the system 10. Larger particles can effectively occlude or clog orifices in the semipermeable tubes of the vacuum degasser unit 21, the ion exchange column, the spectrophotometer, or the fluid lines of the system 10 generally. Such clogging can make the vacuum degasser unit 21, ion exchange column 16, and spectrophotometer 18 less efficient, and can potentially cause back-pressure in the system 10 which is undesirable.

In some embodiments, the filter media 54 can be made of a chemically resistant material such that as the sample 12 passes through the filter media 54 deposits of contaminants from the filter media 54 into the sample 12 can be minimized. In some embodiments, the filter media 54 can be made from a chemically resistant thermoplastic including but not limited to polyether ether ketone (PEEK), or any other suitable polyarytherketone (PAEK). In some embodiments, the filter media 54 once consumed can simply be replaced. However, having a chemically resistant filter media 54 can allow an acid wash to pass through the filter media 54 to clean the filter media 54 of any collected contaminants while not damaging the filter media 54 or introducing reacted contaminants from the filter media 54 into the system 10.

The filter media 54 is shown in FIG. 1 on the suction line 52 of the pump 14. In some embodiments, one or more filter media 54 can be placed in various places within the system 10 to help maximize filtering of larger particles from the sample 12. However, having the filter media 54 generally at the beginning of the flow path of the system 10 can help prevent large particles from contaminating or clogging various pieces of equipment within the system as previously discussed. It can also be beneficial to periodically (semiannually or annually) disconnect the ion exchange column and run a strong acid wash having a concentration of roughly 50 percent strong acid through remaining components of the system 10 to remove any unwanted contaminants that may be deposited in various components of the system 10, and then thoroughly rinse all components of the system with fresh water thereafter.

Description of Method

Samples collected from a liquid source such as a power plant or other boiler steam-generating locations can ideally be collected after any water sampling/conditioning panel of the liquid source/steam boiler system. Since this method and equipment configuration utilizes one or more ion exchange columns, including but not limited to a strong acid cation column (included in the sample flow path), water samples collected before a cation column sampling panel of a liquid source/steam boiler system can also be analyzed, although not preferred.

Water samples received from users for analysis can ideally have no sample preservation. No acids can be added to the sample and care should be taken to not subject the sample to freezing temperatures before or during transport, or prior to analysis. Such preservatives, acids, and/or temperature disparities can affect the integrity and sensitivity of the testing method.

Samples should be collected and analyzed as soon as possible and ideally within a few days of sample collection. Water samples should ideally be collected in new, clean, and rinsed 250 mL HDPE sample bottles. Sample degradation/bottle contamination contributes a false positive error rate of approximately 5 parts per billion per day after initial sample collection.

The sample, once received and prior to analysis, can be brought to typical ambient temperatures (20° C. to 30° C.), accomplished by either external sample warming or cooling, using typical laboratory-based devices such as a temperature bath. In some embodiments, the sample 12 can be placed in a temperature bath of between about 24° C. to 26° C., to bring the temperature of the sample to between about 24° C. to 26° C. In still other embodiments, the sample 12 can be placed in a temperature bath of about 25° C., to bring the temperature of the sample to between about 25° C. Bringing the sample 12 to a consistent temperature can help produce consistent results and test between samples being collected from different locations where temperatures may vary. Once the sample 12 reaches the desired temperature, testing should be done relatively quickly, such as within 10 minutes, to help ensure the sample 12 is tested at as close to the desired temperature as possible.

The flow path through the system 10 and sample 12 aspiration is accomplished by pumping of the sample, for instance using a FillPalMini peristaltic pump. The water sample 12 to be tested is aspirated by the FillPalMini, passed through the first vacuum degasser channel 20 of the vacuum degasser unit 21, and then routed through the ion exchange column 16, or strong acid cation-charged resin column 16. The discharge from the ion exchange column 16 is then passed through the second vacuum degassing channel 22, the discharge of which is then passed through the spectrophotometer 18, and specifically through a flow-through quartz cuvette 34, and then finally, to a drain or waste collection site 58. The quartz cuvette 34 in some embodiments can be a 50 mm quartz cuvette 34, though cuvettes 34 of varying sizes can be utilized.

The start of the method involves aspirating a pure water sample 12 from the water sample 12 collection container using a suitable pump 14, such as a peristaltic pump, at a flow rate of between about 15-25 mL/min for a duration of 90 seconds. In some embodiments, the flowrate of this initial flow stage can be about 20 mL/min. During these 90 seconds, the sample 12 enters the first vacuum degasser channel 20. The sample 12 then flows through the ion exchange column 16, through to the second vacuum degasser channel 22, through the quartz cuvette 34, and finally to drain. This procedure helps remove bulk volatile contaminants and to flush the entire liquid flow path of a previous sample prior to the current sample being tested.

Software program settings on the control unit 40 can then be programmed to change the aspiration and/or pumping rate of the sample 12, decreasing it from 15-25 mL per minute down to between about 6-10 mL per minute, for an additional duration of 240 seconds. In some embodiments, the flow rate of this second stage of the testing procedure can be about 8 mL/min. The sample 12 flow path remains the same as discussed above.

After completing the 240-second sample 12 aspiration, the system 10 can enter a forced sample stand/wait period, for instance a 5-10 second wait period, followed by an immediate initiation of the spectrophotometer's high-powered Xenon light source. The sample 12 can be impacted for a 5-second period with a desired wavelength of light, which in some circumstances can be a full wavelength range of light. The spectrophotometer 18 can take multiple readings and offers a calculated average result. The spectrophotometer 18 can only activate the light source 24 when required and remains on standby when not being used, which extends the lifespan of this core part of the spectrophotometer 18.

A minimum sample volume of 62 mL can be required depending on the size of the cuvette 34 and the established flow rates of the system 10 during the testing. An ideal working solution volume (to allow for repeat sample analysis and/or errors) would be between 200 mL and 300 mL.

All program options, method procedures, timers, method prompts, flow-rates, and calibration slope information are all pre-programmed on the spectrophotometer 18.

Method Interferences

Water samples to be analyzed using this method should ideally be collected after the user's sample conditioning panel cation columns. However, if not available, this method can still be applied to samples collected before the user's cation column sample conditioning panel, as the instrument comes equipped with a strong-acid cation exchange column.

Typical high-pressure power plant, steam-water cycle contaminants were evaluated, namely: phosphates, hydrazine, carbohydrazide, sodium hydroxide, ammonia, ammonium carbamate, formate, acetate and glycolate. The dissociation of these contaminants in the high-temperature cycle, as either cationic or anionic contaminants, is noted.

Since a strong-acid cation exchanger column is utilized, either on the user's sample conditioning panel or in the included equipment configuration, many of the contaminants would merely be exchanged and converted to carbon dioxide (carbonic acid), which would ultimately be liberated by the second vacuum degasser channel 22.

Carboxylic acids, however, would not be removed by the cation column, but are still, in major part, liberated by effective vacuum degassing. These interferences were analyzed for their contribution under typical cycle chemistry conditions, listed below:

Ammonium hydroxide—no interference at any concentration.

Formate—no interference at concentrations <1000 parts per billion.

Acetate—no interference at concentrations <250 parts per billion.

Glycolate—no interference at concentrations <100 parts per billion

Thus, although there have been described particular embodiments of the present invention of a new and useful TESTING METHOD FOR RESIDUAL ORGANIC COMPOUNDS IN A LIQUID SAMPLE, it is not intended that such references be construed as limitations upon the scope of this invention.

What is claimed is:

1. A method of testing a water sample for at least one anti-corrosion saturated and/or unsaturated aliphatic nitrogen containing organic compound, the method comprising the steps of:
   collecting the water sample from a thermal power system or other steam water cycle;
   passing the water sample through an ion exchange column;
   passing the water sample through a first vacuum degassing channel after passing through the ion exchange column;
   transmitting light having a wavelength in the UV Spectrum into the water sample;
   measuring absorption/transmission of the light by the at least one saturated and/or unsaturated aliphatic nitrogen containing organic compound in the water sample;
   determining a concentration of the at least one saturated and/or unsaturated aliphatic nitrogen containing organic compound within the water sample based on the absorption/transmission of the light in the UV Spectrum by the at least one saturated and/or unsaturated aliphatic nitrogen containing organic compound.

2. The method of claim 1, wherein the method is a reagent/indicator free testing method, and further comprises measuring light absorption directly by the at least one saturated and/or unsaturated aliphatic nitrogen containing organic compound in the water sample.

3. The method of claim 1, wherein the thermal power system is a steam boiler.

4. The method of claim 1, further comprising the step of filtering the water sample using a 0.1 to 0.3 micron filter prior to transmitting light into the water sample.

5. The method of claim 1, further comprising the step of bringing the temperature of the water sample to between 24 degrees Celsius and 26 degrees Celsius prior to transmitting light through the water sample.

6. The method of claim 5, wherein the temperature of the water sample is brought to between 25 degrees Celsius and 26 degrees Celsius prior to transmitting light through the water sample.

7. The method of claim 1, wherein light is transmitted through the water sample and the absorption of light by the at least one saturated and/or unsaturated aliphatic nitrogen containing organic compound in the water sample is measured using a spectrophotometer.

8. The method of claim 7, further comprising the steps of:
   pumping the water sample through the ion exchange column, the first vacuum degassing channel, and the spectrophotometer; and
   passing the water sample through the ion exchange column and the first vacuum degassing channel prior to transmitting light into the water sample.

9. The method of claim 8, wherein the ion exchange column is a strong acid cation exchange column.

10. The method of claim 9, wherein:
    the method further comprises passing the water sample through a second vacuum degassing channel before the water sample is passed through the strong acid cation-charged resin column and prior to transmitting light into the water sample.

11. The method of claim 10, further comprising the step of passing a strong acid solution having a concentration of between 2 percent and 10 percent through the first and second vacuum degassing channels, the strong acid cation-charged resin column, and the spectrophotometer on a daily basis.

12. A system for measuring the concentration of at least one anti-corrosion saturated and/or unsaturated aliphatic nitrogen containing organic compound in a water sample from a thermal power system or other steam water cycle, the system for measuring comprising:
    a pump for pumping the water sample through the system fro measuring;
    an ion exchange column in fluid communication with the pump;
    a first vacuum degasser channel in fluid communication with the ion exchange column; and a spectrophotometer in fluid communication with the ion exchange column via the first vacuum degasser channel, the spectrophotometer configured to transmit light having a wavelength in the UV spectrum into the water sample and measure the absorption/transmission of the light in the UV Spectrum by the at least one saturated and/or unsaturated aliphatic nitrogen containing organic compound in the water sample.

13. The system of claim 12, wherein the ion exchange column is a strong acid cation-charged resin column.

14. The system of claim 12, further comprising a second vacuum degasser channel in fluid communication between the ion exchange column and the pump such that the ion exchange column is in fluid communication with the pump via the second vacuum degasser channel.

15. The system of claim 14, wherein the first and second vacuum degasser channels are contained in a single vacuum degasser unit.

16. The system of claim 12, wherein the pump includes a suction inlet including a 0.1-0.3 micron filter media oriented such that the water sample passes through the filter media as the water sample is pumped through the system.

17. The system of claim 16, wherein the filter media comprises a chemically resistant thermoplastic.

18. A system for measuring the concentration of an organic compound in a liquid sample, the system comprising:
- a pump for pumping the liquid sample through the system;
- a vacuum degasser unit having a first vacuum degasser channel and a second vacuum degasser channel, the first vacuum degasser channel in fluid communication with the pump;
- a strong acid cation ion exchange column in fluid communication between the first vacuum degasser channel and the second vacuum degasser channel; and
- a spectrophotometer in fluid communication with the second vacuum degasser channel, the spectrophotometer configured to transmit light having a wavelength of 190 nanometers to 310 nanometers into the liquid sample and measure the absorption/transmission of the light by the organic compound in the liquid sample.

* * * * *